(12) United States Patent
Wareham et al.

(10) Patent No.: US 7,131,341 B2
(45) Date of Patent: Nov. 7, 2006

(54) METHOD AND APPARATUS FOR DETECTION OF TRACE VOLATILES

(75) Inventors: Peter Darren Wareham, High Peak (GB); Krishna Chandra Persaud, Cheadle (GB)

(73) Assignee: Peter Cox Limited, Sutton (GB)

( * ) Notice: Subject to any disclaimer, the term of this patent is extended or adjusted under 35 U.S.C. 154(b) by 0 days.

(21) Appl. No.: 11/254,651

(22) Filed: Oct. 20, 2005

(65) Prior Publication Data

US 2006/0123931 A1    Jun. 15, 2006

(30) Foreign Application Priority Data

Apr. 30, 2003  (GB)  ................. 0309824.1

(51) Int. Cl.
*G01N 1/04*    (2006.01)

(52) U.S. Cl. .................................. 73/864.71

(58) Field of Classification Search ............ 73/864.71, 73/864.21, 864.81, 864.83
See application file for complete search history.

(56) References Cited

U.S. PATENT DOCUMENTS

| | | | | |
|---|---|---|---|---|
| 5,345,213 | A | 9/1994 | Semanik et al. | 338/34 |
| 5,691,206 | A * | 11/1997 | Pawliszyn | 436/178 |
| 5,859,362 | A | 1/1999 | Neudorfl et al. | 73/23.2 |
| 6,354,135 | B1 * | 3/2002 | McGee et al. | 73/23.34 |
| 6,397,658 | B1 * | 6/2002 | Villettaz et al. | 73/19.12 |
| 6,405,608 | B1 | 6/2002 | Lindgren et al. | 73/863.21 |
| 6,477,907 | B1 | 11/2002 | Chambers et al. | 73/866 |
| 6,537,827 | B1 | 3/2003 | Pawliszyn | 436/178 |
| 6,825,046 | B1 * | 11/2004 | Forsyth | 436/178 |
| 6,941,825 | B1 * | 9/2005 | Pawliszyn | 73/864.87 |

FOREIGN PATENT DOCUMENTS

| | | |
|---|---|---|
| GB | 2297381 | 3/2003 |
| JP | 04-015553 | 4/1992 |
| WO | WO 01/57515 | 8/2001 |

\* cited by examiner

*Primary Examiner*—Daniel S. Larkin
*Assistant Examiner*—Tamiko Bellamy
(74) *Attorney, Agent, or Firm*—Gauthier & Connors, LLP

(57) ABSTRACT

A method and apparatus for the detection of trace volatiles such as those produced by fungal decay of timber, comprising a sampling probe (10), comprising a housing (11) and bored barrel (12) adapted removably to receive an SPME device (14) in which a coated tipped fiber (15) is guided within a needle sheath (16) into the barrel (12), and a pump (19) is energized to draw a fluid sample over the fiber tip within the bore of the barrel. A motor (23) advances and retracts the SPME device (14) and its fiber (15) for a sample to be captured thereby and the captured sample is then released within an instrument having an array of gas sensors whereby any trace volatiles captured by and released from the coated fiber (15) may then be analyzed by computer software to produce a fingerprint for the location and identification of the presence of trace volatiles at a site into which the sampling probe is introduced. Thus, there is provided a robust device for the protective and easy introduction of an SPME fiber into a sampling environment where such devices conventionally could not be used.

14 Claims, 7 Drawing Sheets

METHOD AND APPARATUS FOR DETECTION OF TRACE VOLATILES

PRIORITY INFORMATION

The application claims the benefit of Great Britain Application Serial No. 0309824.1, filed on Apr. 30, 2003, and International Patent Application Serial No. PCT/GB2004/001849 filed on Apr. 29, 2004.

BACKGROUND OF THE INVENTION

THIS INVENTION concerns a technique and an instrument for on-site detection of trace volatiles, in gaseous, vapour or liquid phase, particularly, though not exclusively, those generated by timber decay fungii.

Fungal attack of construction timbers can progress, sometimes unnoticed, to a state where the timber is weakened sufficiently to compromise building safety. The fungus which results in dry-rot is *Serpula lacrymans* which grows readily in areas such as cellars, behind panelling and plaster, and in sub-floor spaces thus making it difficult to detect the presence of such fungus at an early stage.

It is therefore an object of the present invention to provide a method of and instrument for the detection of such fungus to provide an aid to early diagnosis thus minimising costs associated with fungal damage and disruption caused by remedial investigations.

Odours emitted from wood-rotting fungus comprise defined volatile organic compounds which are indicative of fungal infection on timber. A distinctive mushroom-like odour accompanies *Serpula lacrymans* growth. The mushroom-like odour is derived from a complex mixture of trace volatiles, some of which may be used as unique markers for detection of *Serpula lacrymans*.

The method and instrument described herein is intended particularly, though not exclusively, for the detection of dry-rot fungus but may be adapted for use also in the detection of other fungal species and of pest infestations such as are caused by rats, cockroaches and termites, since such pests also give off odours or trace volatile chemicals. Indeed, there are many potential applications for the present invention, where trace volatiles are present in gaseous, vapour or liquid phase, and can be detected using the present method and instrument, simply modified to detect the appropriate chemical odour.

As a matter of practicality it is also an object of the present invention to provide an instrument which may be used by semi-skilled personnel or property surveyors in the field, the instrument being portable and thus capable of being deployed, without damage, in the most cramped and inaccessible of sites.

The instrument will be used in conjunction with computer software including mathematical algorithms which when applied to signals generated by the instrument will produce a response which effectively provides a fingerprint for the location and identification of the presence of trace volatiles, even in the presence of background odours.

The instrument may include known technology employing an array of commercially available sensors coupled to electronic apparatus for data acquisition and analysis.

The discriminatory capability of sensor arrays relies upon the utilisation of cross-sensitivities between individual sensors. In such an array the individual sensors possess slightly different responses to odour volatiles, and these differences provide sufficient information to discriminate between different odour volatiles. Such an array of sensors combined with electronic analytical computer equipment and suitable mathematical methods may be referred to as an "electronic nose". Typically, such a device consists of three elements, namely, the sensor array which is exposed to the trace volatiles, means for conversion of the sensor outputs to a readable format and means to perform software analysis of the data to produce a fingerprint representative of a particular set of trace volatiles. The output from the sensor array may be interpreted via a variety of methods such as pattern recognition algorithms, principal component analysis, discriminant function analysis, cluster analysis and artificial neural networks to discriminate between samples.

A variety of sensor types may be adopted, for example, quartz crystal sensors in which the crystal oscillates in an electrical field and its change of frequency, brought about by the presence of trace volatiles, can be measured. Other kinds of sensor include surface acoustic wave sensors including a piezo-electric substrate onto which is deposited a thin film coating of a selective material. An applied radio frequency voltage produces a surface acoustic wave on such material, and adsorption of odour volatiles onto the coating increases its mass and disturbs the wave leading to a shift in frequency, which can be measured. Another type of sensor may be taken from several available types of resistive sensors and in this particular example the preferred type is a metal oxide semiconductor sensor whose electrical resistance changes in the presence of odour volatiles. Such sensors also have the advantage that they perform as heaters whereby the ambient temperature within a chamber containing an array of such sensors may be elevated to cause trace volatiles to be desorbed from a carrier coating.

In a typical environmental application, the consistent collection and delivery of odour volatiles into an "electronic nose" may be problematic. A number of factors contribute to this, namely inherent environmental variables such as temperature and humidity, and physical parameters such as site accessibility and air-borne particulates such as dust. Also, site-specific background interference odours and low concentration target volatiles may contribute to the complexity of the detection technique.

SUMMARY OF THE INVENTION

According to a first aspect of the invention, there is provided an instrument for detecting the presence of trace volatiles, comprising a sampling probe having a receptor adapted protectively to receive a coated fibre of a solid phase microextraction device (SPME) for introduction to a site to be sampled, the sampling probe including means associated with the receptor to direct a fluid stream from the site over the SPME fibre located within the receptor thus to cause one or more trace volatiles to be captured by the fibre coating, the instrument further comprising a data acquisition device having an array of gas sensors contained within a chamber adapted to receive said coated SPME fibre having one or more trace volatiles captured thereby, means for causing said one or more trace volatiles to be released from the fibre coating into the chamber such that in use the gas sensors may detect said one or more trace volatiles released from the SPME fibre, and means responsive to the sensors to produce one or more signals identifying said one or more trace volatiles captured by and released from the SPME fibre.

The receptor may be maintained at ambient temperature during capture of said one or more trace volatiles.

The gas sensors may be metal oxide semiconductor gas sensors which, in use, undergo individual changes in electrical resistance representative of said one or more trace volatiles.

The sampling probe may include a dust or other contaminant filter to prevent such contaminants from alighting upon the SPME fibre coating and to prevent non-specific capture and loss of trace volatiles of interest for the detection procedure.

The receptor may include a fibre guide to centralise the SPME fibre within a tubular barrel.

The tubular barrel may include a threaded portion for attachment of the contaminant filter or, selectively, an additional length of barrel.

The fluid stream direction means may include a pump connected to the receptor.

The receptor may be formed as a housing adapted removably to receive the SPME device.

The housing may include means therein to manoeuvre the SPME fibre thus to advance and retract the fibre selectively within the receptor.

The means for causing said one or more trace volatiles to be released from the SPME fibre may comprise a plurality of individual heaters each associated with one of the gas sensors. Additional heaters may be incorporated to optimise the release characteristics of the device.

Means may be provided automatically to retract the fibre within a needle sheath of the SPME device prior to or upon removal from the receptor.

Means may be provided, where samples are to be taken at a plurality of locations, to link or identify an SPME fibre, after sampling, with an associated sampling probe or location thereof.

Means may be provided to determine and record the duration of a sampling period and/or of the number of samples taken by an individual SPME fibre.

According to a further aspect of the invention there is provided a method of detecting the presence of trace volatiles, comprising the steps of introducing a coated SPME fibre contained protectively within a receptor of a sampling probe, to a site to be sampled, and directing a fluid stream over the SPME fibre within the receptor thus to cause any trace volatiles present at the site, to be captured by the fibre coating; introducing the SPME fibre into a data acquisition device having a chamber containing an array of gas sensors; causing one or more captured trace volatiles to be released from the SPME fibre; and producing one or more signals identifying said one or more trace volatiles captured by and released from the SPME fibre.

An embodiment of the invention will now be described, by way of example only, with reference to the accompanying drawings, in which:

Figure 1:
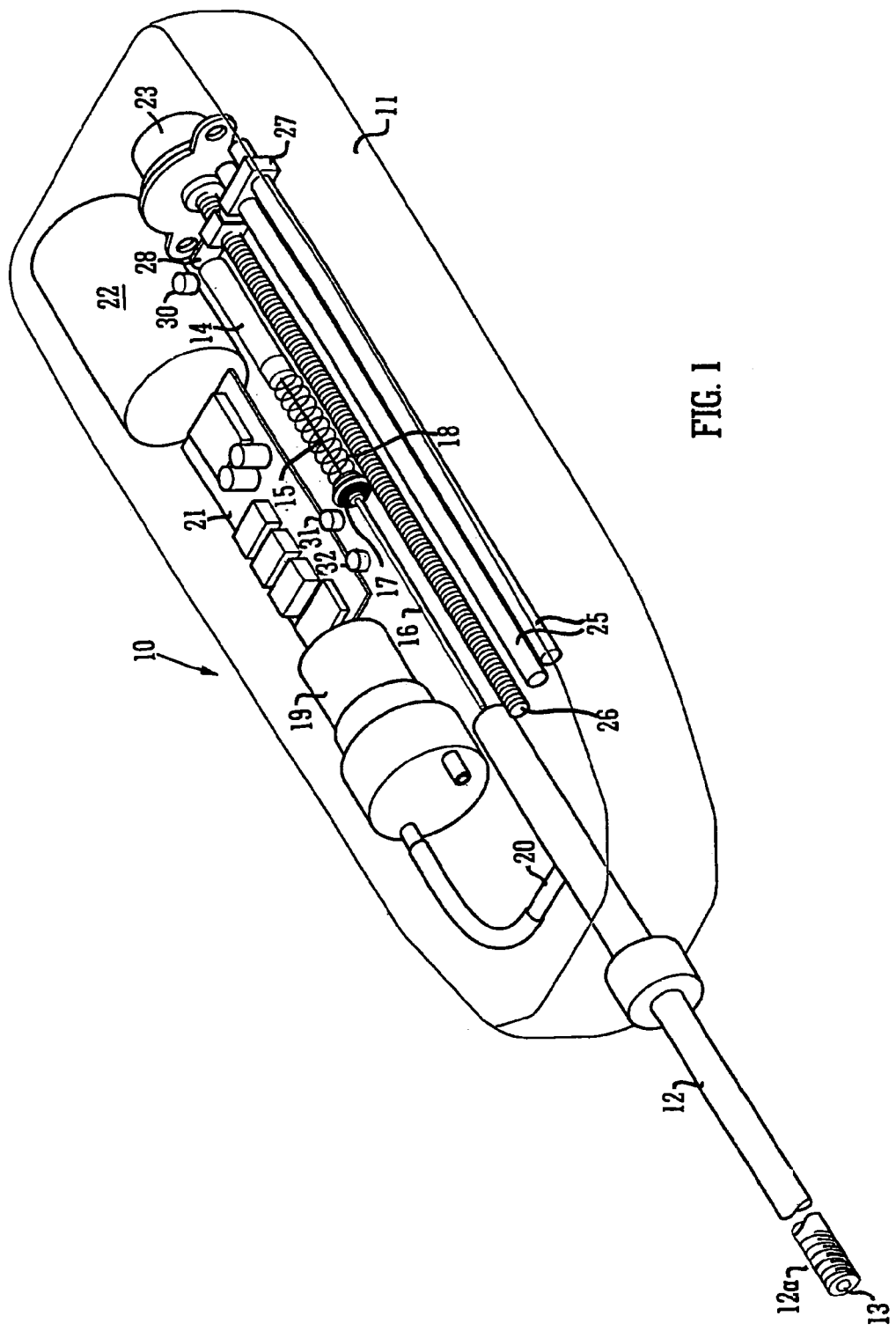
FIG. 1 is a schematic perspective view of a sampling probe which may form part of the instrument in accordance with the present invention.

A commercially available SPME device consists of two parts. Centrally there is provided a fibre contained within a hollow needle sheath. At the tip of the fibre is a length of bonded coating material which adsorbs or absorbs volatile species enabling a sample to be retained temporarily on the tip.

DESCRIPTION OF THE INVENTION

The bonded coating may be a liquid (polymer) phase or a solid (sorbent) phase, or a combination of both. Trace volatiles are extracted by absorption in the case of liquid phase coatings, or by adsorption in the case of solid phase coatings, or a combination for hybrid coating types. An example of an adsorptive liquid phase coating at a thickness of 100 microns is polydimethylsiloxane (PDMS). An example of an adsorptive solid phase coating at a thickness of 65 microns is carbowax-divinylbenzene (DVB).

The fibre retracts within the needle sheath for mechanical protection. The fibre is exposed and retracted selectively for sampling, and sample delivery, by a fibre holder which is spring-loaded normally to retain the fibre within the needle sheath, but it may be advanced against the action of the spring to expose the fibre tip. Such a device is well known and not claimed herein, per se, as novel. Commercially available SPME devices are not readily adaptable for deployment in a physically difficult sampling environment, owing to the fragility of the fibre and needle sheath and the need to ensure repeatable sampling, which therefore cannot be achieved directly using the device alone. An SPME device has no facility for filtering air-borne contaminants such as dust which could lead to fibre contamination, and possesses no robust user interface to enable effective SPME deployment by unskilled operatives in the field.

Referring now to FIGS. 1 to 7 a sampling probe 10 made in accordance with the invention comprises a body or housing 11 from one end of which extends a tubular barrel 12 having an external screw thread 12a at its remote open end. The barrel extends part way into the housing 11 and defines a central bore 13.

The housing 11 has a hinged door (not shown) for gaining access to the interior thereof thus to introduce into the housing an SPME device which consists of a holder 14, a fibre 15 attached to and extending from one end of the holder 14 and a needle sheath 16 having a sealing ring 17 and a spring 18 located between the needle sheath 16 and holder 14 thus normally to maintain the holder and needle sheath at a predetermined fixed disposition. As in commercially available SPME devices, the holder 14 and needle sheath 16 are contained within a tubular body (not shown) whereby, upon compression of the spring 18, the fibre 15 is advanced along the bore of needle sheath 16.

The housing 11 also contains an air or other fluid pump 19 connected at 20 to the barrel 12 and communicating with the central bore 13 thereof.

The housing 11 also contains a printed circuit board and components 21 and battery 22.

Located alongside the battery 22 within the housing 11 is an electrically driven (from the battery) stepper motor 23 to which is attached a frame 24 (FIG. 2) which retains a pair of guide rods 25 and one end of a threaded rod 26 the other end of which is connected to and driven by the stepper motor 23.

Slidably mounted on the guide rods 25 and threadedly engaged upon the rod 26 is a carriage 27 from which extends a magnetic tab 28. As will be seen, when the carriage 27 is advance along the threaded rod 26 by rotation thereof, the tab 28 is also advanced to make magnetic contact with a rear face of holder 14 of the SPME device to advance it towards the left-hand end of FIG. 2.

Position sensors 30, 31 and 32 which may be magnetic, interface with the tab 28 to provide an indication, as will be described, of the instantaneous position of the tab 28 and thus the SPME device during operation of the probe. An identification tag 33 may be provided on the holder 14 thus to identify an individual SPME device.

Figure 2:
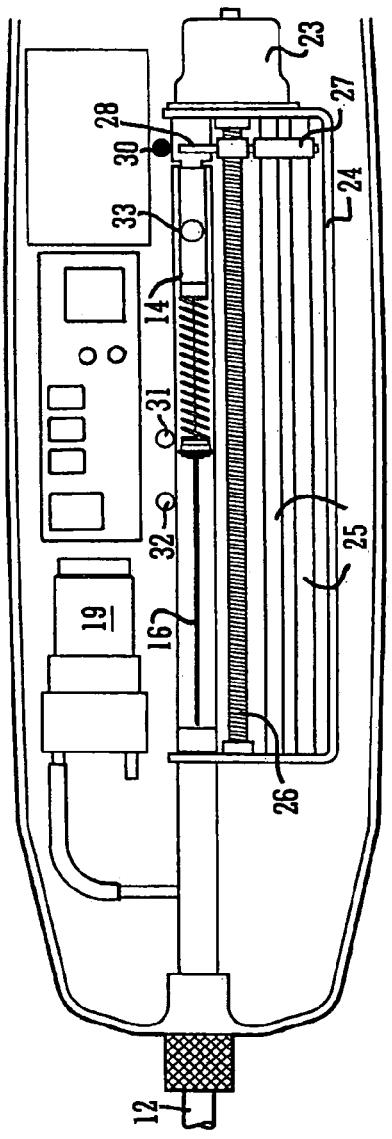
FIGS. 2 to 4 illustrate three operational modes of the sampling probe of FIG. 1.

Operation of the probe will now be described with reference to FIGS. 2 to 4 in which FIG. 2 illustrates the positions occupied by the moving parts of the probe, before and after a sampling cycle. In this position carriage 27 and tab 28 are at their rearmost position in the housing 11, and this is detected by sensor 30 which, by way of the components on the PCB 21 and the electrical supply thereto from battery 22, may be displayed by an LED indicator (not shown) on the housing 11.

Any suitable switching device is provided to energise the stepper motor 23 thus to advance the carriage 27 and tab 28 towards the left-hand end of FIG. 2.

Figure 3:
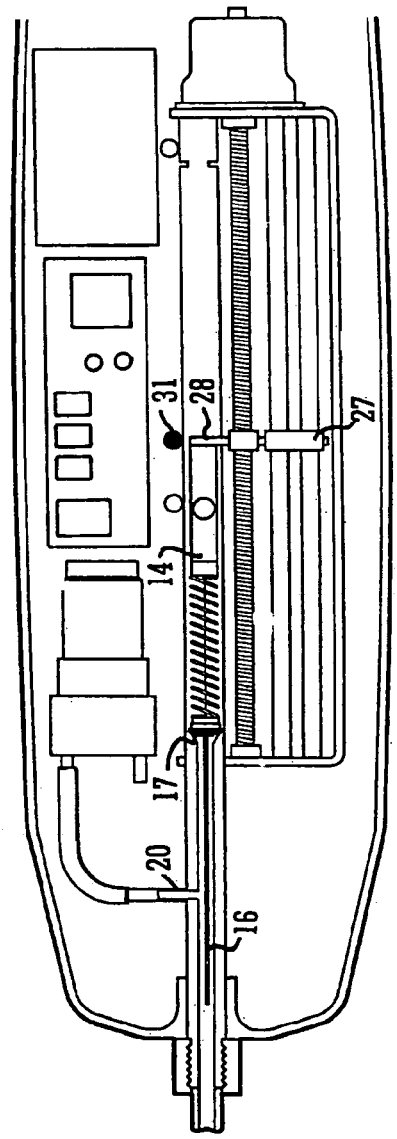

FIG. 3 illustrates a position in which tab 28 has advanced holder 14 and needle sheath 16 to a position in which the sealing ring 17 has located against a tapered introductory face of the central bore 13 of the barrel 12. This position is detected by sensor 31 and tab 28 thus to provide a further indication by LED display.

With the parts located as shown in FIG. 3 air pump 19 may be operated to draw air through the bore 13 of barrel 12, to purge the system.

Figure 4:
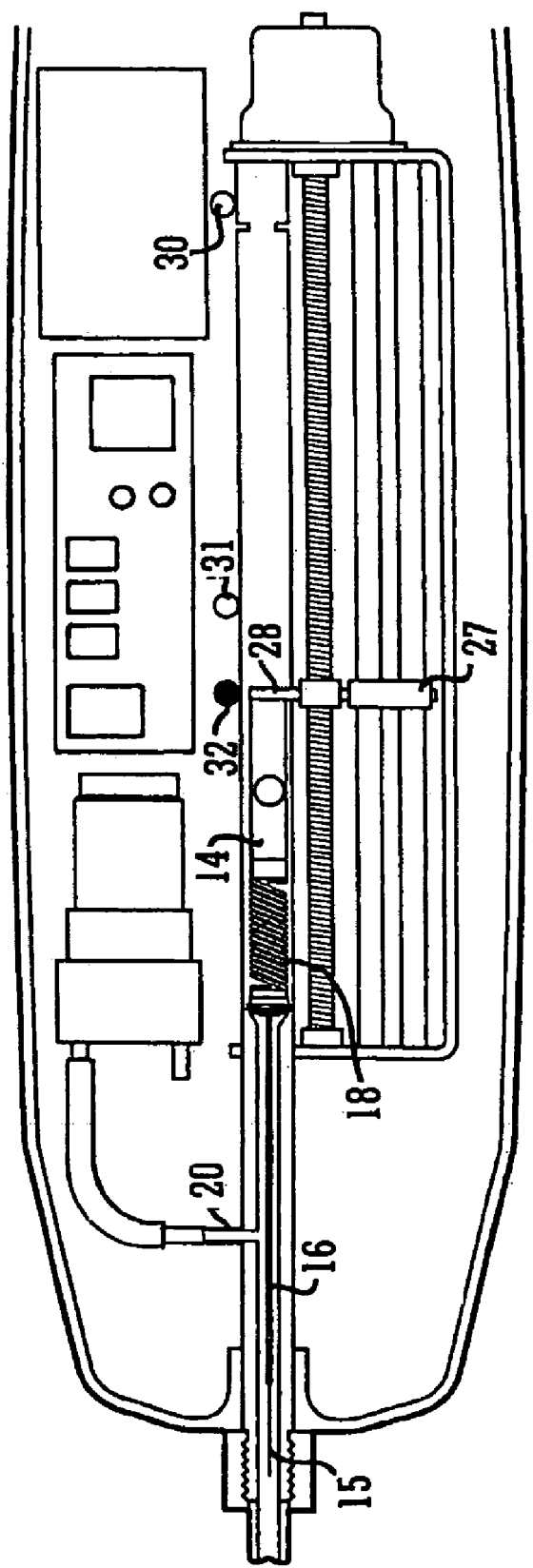

Referring now to FIG. 4, when it is required to take a sample, motor 23 is energised once again to advance holder 14 and fibre 15, against spring 18, until the coated fibre tip is exposed beyond the remote end of needle sheath 16, within bore 13. This position may be detected by sensor 32 and tab 28 thus to energise a further LED display.

With the parts positioned as illustrated in FIG. 4, air pump 19 may be energised to draw air or other fluid inwardly through central bore 13 from the remote end thereof thus entraining trace volatile chemicals which impinge upon the fibre tip which, according to its coating, will adsorb or absorb the trace volatiles. After a selected period, typically a few minutes, the stepper motor 23 is rotated in reverse to withdraw the fibre tip within the needle sheath 16 and to withdraw the SPME device to the position illustrated in FIG. 2. Thus, the sample is complete and the SPME device may be removed from the housing 11 to be introduced into a data acquisition device as will be described.

Figures 5, 6, 7:
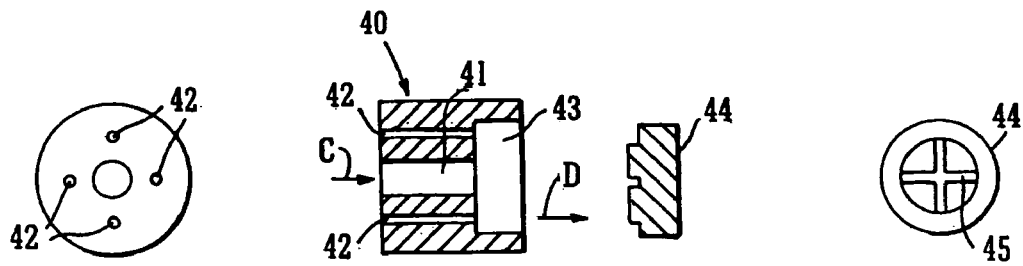
FIG. 5 is a schematic cross-sectional exploded view of a dust filter attachable to the sampling probe.
FIG. 6 is a view taken on arrow C of FIG. 5.
FIG. 7 is a view taken on arrow D of FIG. 5.

Referring now to FIG. 5 to 7, a dust filter 40 has a central internally threaded bore 41 thus to be screwed onto the screw threaded portion 12a at the remote end of the barrel 12 of the probe, and contains an array of micro-bores 42 through which ambient air or other fluid may pass into a recessed portion 43 which is adapted to receive a removable plug 44 which has, on its surface to be disposed at the base of the recess 43 an arrangement of cross channels 45 which thus permit the ambient fluid to travel from the micro-bores 42 and into the bore 13 of the barrel 12 of the probe. The plug 44 thus filters the incoming fluid, and is removable for cleaning.

This is just one example of filter which may be applied to the probe and uses the principle of a convoluted path for the fluid stream. Alternatively, or in addition, a filter using replaceable filter packing may be used. The packing is selected to minimise or prevent non-specific capture and loss of volatiles of interest.

The threaded portion 12a of the barrel 12 alternatively or additionally permits the attachment of an additional length of barrel if required for further reach.

In use, the sampler is deployed by introducing the barrel 12 (with its filter) into the immediate location of interest, typically between courses of bricks, cavity walls and sub-floor spaces. The SPME fibre 15 is advanced, by motor 23, within the sampler and the pump 19 is energised such that the SPME fibre is exposed within the bore 13 of the sampler to capture odour components from the sample fluid stream. At the end of the required sampling time the SPME fibre is retracted and the SPME device is removed from the sampling probe which, however, may remain in-situ for repeated samples to be taken, or may be removed to another location.

The tag 33, on the SPME holder 14, in conjunction with suitable electronics serves to identify the particular SPME fibre and to count the number of exposures to which that fibre is subjected during its lifetime as well as the period of each exposure.

In order to ensure that the SPME fibre is not damaged during or subsequent to a sampling cycle, the sensors 30–32 may operate an interlock to ensure that the housing 11 remains closed until the fibre 15 is fully retracted within the needle sheath 16.

Multiple fibre deployment as would be required in a typical site investigation, requires traceability of individual fibres against their respective sampling locations. Therefore, unique identification of each fibre is required which can be recognised against the location in which the sample has been taken. Information encoding using a method such as a bar code, in place of tag 33, may be used for this purpose with associated readers mounted on PCB 21 and the data acquisition device. SPME devices have a finite operational lifetime which if exceeded can produce erroneous sampling characteristics and so a record of individual fibre exposure counts is required, a counter on PCB 21 preferably being linked to a warning indicator on the housing 11 to provide a visual or audible warning to advise of the requirement for fibre replacement before the operational lifetime is exceeded and before a sample is taken.

Fibre exposure time is a factor of SPME sampling such that a minimum sampling time is required. A countdown timer, with preset limits may be linked to the exposure counting sensor for the fibre thus providing an audible and visual alert when the sampling time has elapsed. This timing system may be used also to control switching of the pump 19 and, preferably, automatic fibre retraction at the end of a sampling cycle.

Figure 8:
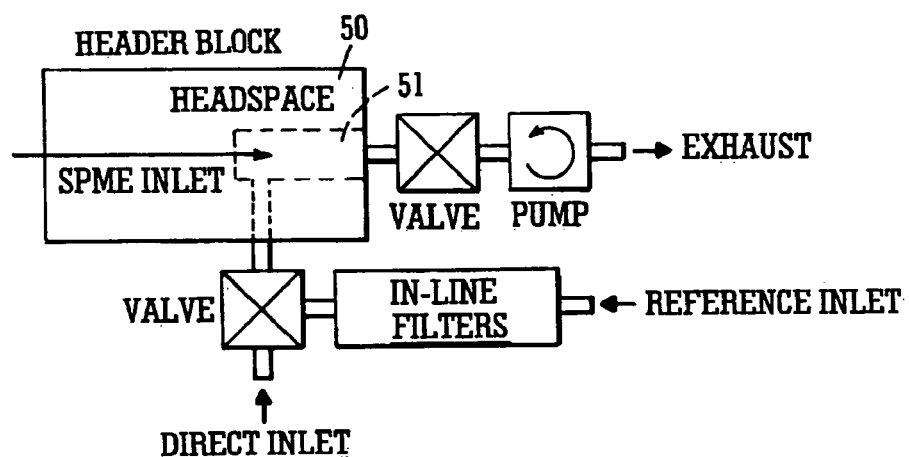
FIG. 8 is a schematic illustration of a data acquisition device being part of the instrument in accordance with the invention.

Referring now to FIG. 8 there are shown the main components of a part of the instrument adapted to acquire the data representative of the presence and identity of trace volatiles captured by the SPME fibre. The instrument contains a body 50 defining an internal head space 51 into which the SPME fibre, after exposure to the trace volatiles may be inserted. Within the head space 51 is provided an array of (in this example) metal oxide semiconductor gas sensors each with its own heater, and coupled to electronics for the data acquisition using an external portable computer for data analysis. The sensors are mounted in a symmetrical 3-dimensional array within the head space 51 which is heated rapidly to an elevated temperature by the sensor heaters.

Alternatively, external heat sources may be used. At this elevated temperature the sample volatiles are desorbed directly into the enclosed region around the sensors. Metal oxide semiconductor gas sensors individually undergo a change in their inherent electrical resistance dependent upon the gases present. Each sensor will detect a particular chemical or range of chemicals, and their individual "ranges" of detection overlap to a degree.

Within the instrument which, in effect, provides an "electronic nose" electronics are used for the interrogation of the sensors and will be custom designed based on a resistance measurement circuit. Preferably, sensor measurement and sensor heater control circuits are integrated on a single PCB. Additionally, a micro-controller is used to provide an interface to an external computer system so that the instrument may be operated in conjunction with a PC (laptop or desktop) or a hand-held platform.

Figure 9:
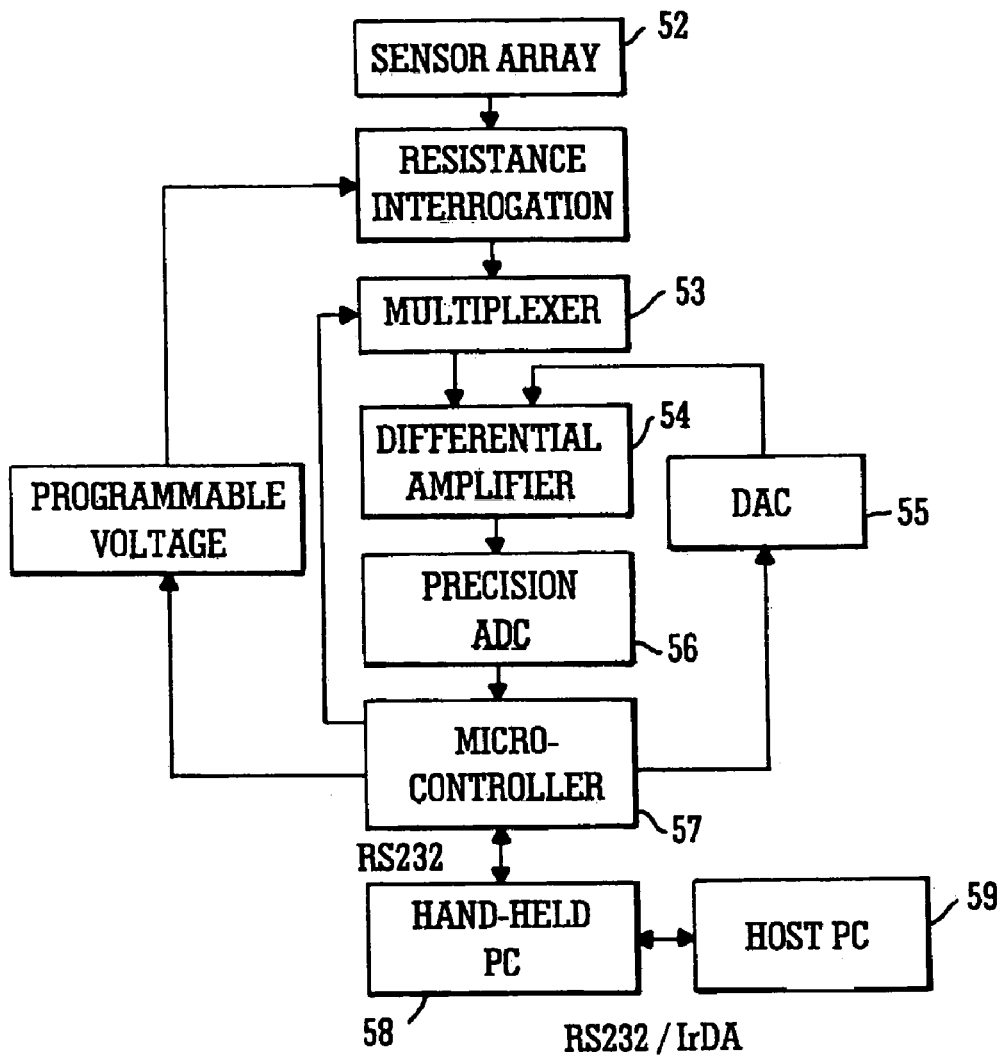
FIG. 9 is a diagram illustrating the main components of the data acquisition device.

FIG. 9 illustrates the principal operational components of the instrument which provides eight channels of analogue data from the gas sensor array 52 which need to be analysed and digitised. The strategy is to sample each input channel sequentially by a multi-plexer switch 53, setting the gain of the amplifier to unity so as to measure the base resistance of each sensor in clean air at the start of a measurement. The digitised values are stored in memory. The data to be subsequently collected are changes in resistance which occur when the sensors respond to volatile chemical species. The stored base resistance values are used individually as an input to the amplifier 54 via a digital to analogue converter (DAC) 55. The output from the offset amplifier is essentially an auto-zeroed output. This signal is then amplified via a programmable gain amplifier before being digitised using a 12-bit analogue to ditigal converter (ADC) 56. A microcontroller 57 handles the control of data sampling at regular intervals, which may be used as defined, and transmits data to an external computer 58 via a serial link (RS232 protocol). Default parameters for heater settings, gain settings and time intervals may be stored in the permanent memory for initialising of this system at the start of operation. A further external computer 59 includes software for processing the raw data to produce, for example, a strip chart for display to the user, and further processing for pattern recognition based on the raw data.

The gas sensors undergo a change in electrical resistance upon adsorption of a gas released from the SPME fibre, and this change is reversible. Care needs to be taken to avoid passing large currents through the sensors themselves and also to control the maximum voltage applied across the sensors. The circuit is based upon passing current through the feedback loop of an operational amplifier The sensors need to be heated to a temperature in the order of 300–400° C. so that they shall be active as gas sensors. The temperature of each sensor determines its sensitivity and selectivity. It is required that the sensors may be individually programmed in an array to different temperatures.

Figure 10:
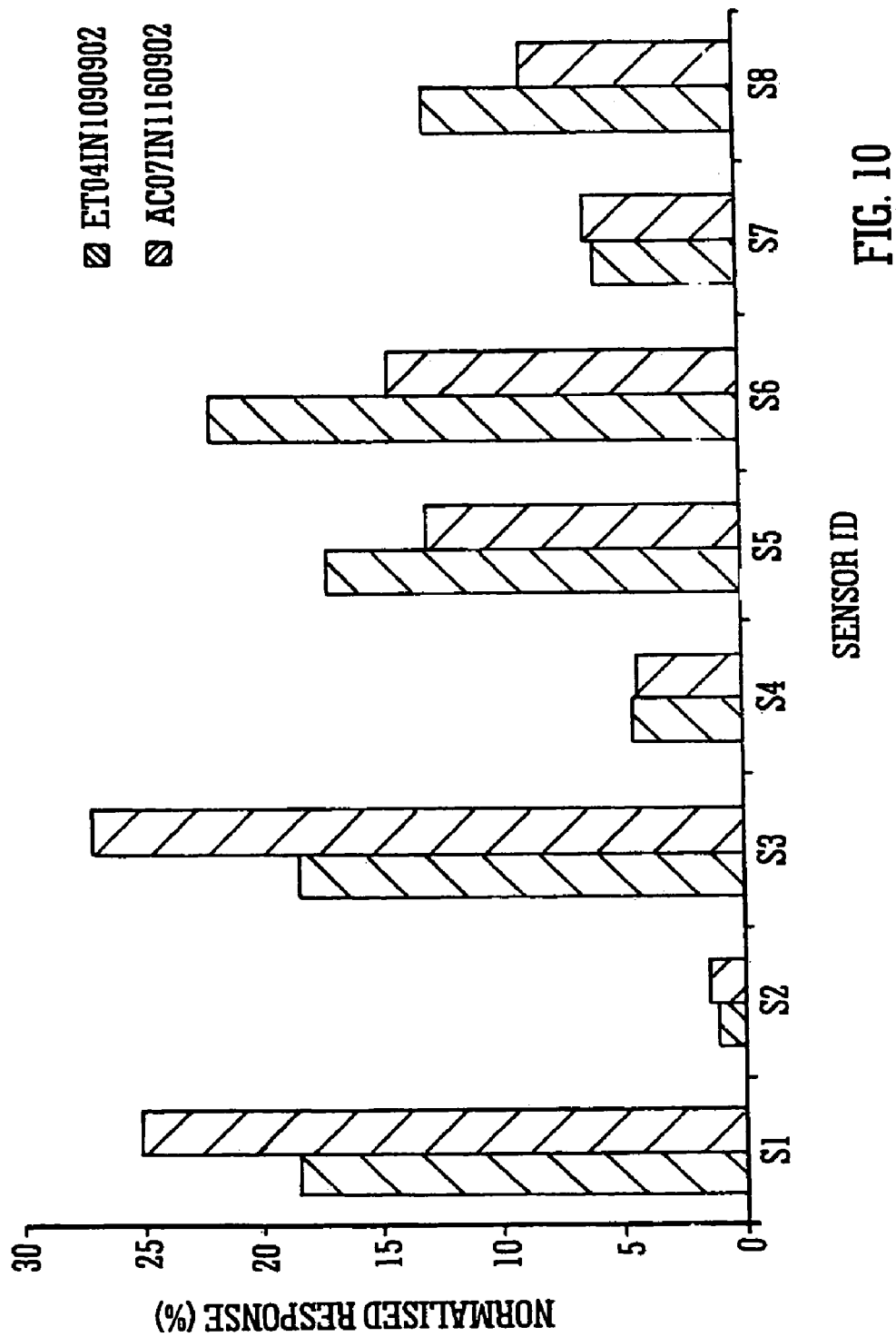
FIG. 10 is a histogram illustrating a typical sensor response profile obtained from the instrument.

In the instrument, data is acquired at a rate of one measurement (of all eight sensors) per second. This gives sufficient resolution to enable detailed analysis of sensor response profiles. The raw output from the sensor array is processed in a number of stages. FIG. 10 shows the basis for discrimination between sample types. Here, the raw sensor responses to two different chemical samples have been normalised and compared. Normalisation produces a pattern which is effectively independent of concentrations of volatiles to which the sensor is responding.

The histogram of FIG. 10, shows the normalised response levels for each sensor in the array. The response levels are compared for the two samples and the observed differences between response levels forms the basis for discrimination between the two samples. Overall, the individual sensor responses form a pattern, which is used for recognition of a particular sample. These patterns are fed into neural networks for machine-based decision making.

The response profiles may be analysed off-line or alternatively algorithms may be included within the acquisition software to enable automatic processing and display of results in a format suitable for general use.

Data processing encompasses a number of separate steps to enable classification of odours from the raw response profiles. Initially, the raw sensor responses are subjected to the normalisation process thus to make separate measurements comparable by accounting for factors such as concentration differences between samples and pre-selectable instrument parameters e.g. electronic and software gain settings, and the like.

Secondly, portions of the normalised responses are further processed to give, in this instance, an averaged normalised response level between selected portions of the response timeline.

Figure 11:
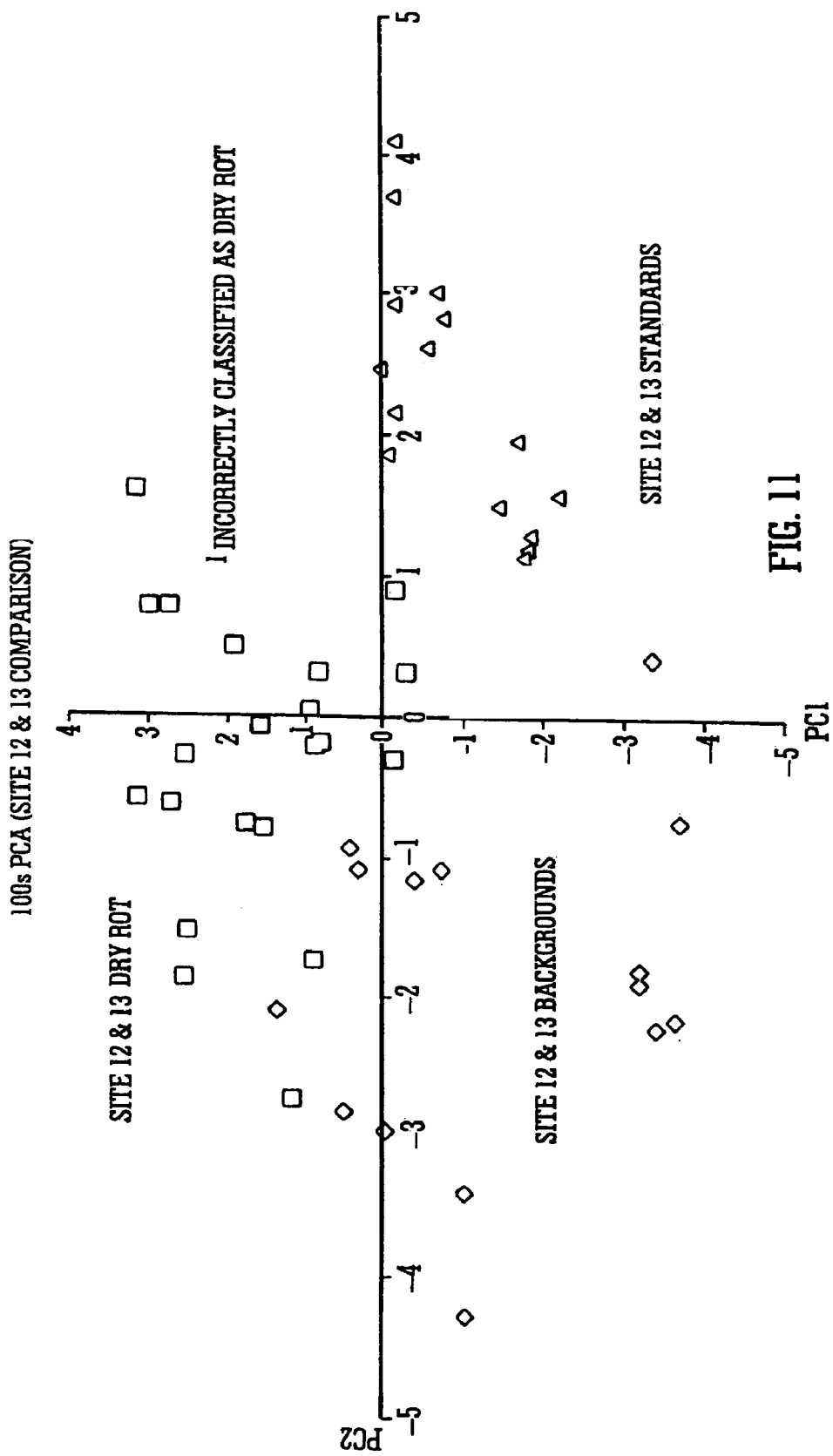
FIG. 11 illustrates principal component analysis (PCA) of trace volatiles detected by the instrument.

When many response patterns are compared, it is difficult to visualise differences between sample types using histograms alone. Instead, principal components analysis (PCA) is used, which is a method of reducing multi-dimensional data to lower dimensions based on the variance between individual patterns. FIG. 11 uses PCA on data obtained at two site visits where dry rot was investigated. What is observed is a general clustering or grouping of data points in areas of the graph according to the type of sample. This indicates that defined differences in sensor response patterns to each sample type are present, which may be used as a basis for recognition and classification of sample type. Thus, if a sensor response pattern for an unknown sample were to lie in an area of the graph bounded by points of a known sample, it is possible to predict with a certain probability what that unknown sample is likely to be, based on previous knowledge.

The invention achieves a readily usable and physically robust instrument operable to detect the presence of trace volatiles in a potentially inaccessible environment which is hostile to precision instrumentation, by providing a sample probe which is adapted readily to receive an SPME device and wherein the latter may be transposed into data acquisition instrumentation after removal from the immediate sample site thus to produce, rapidly and simply, a result indicative of the presence of trace volatiles such as those experienced in the region of timbers infected with dry-rot fungal decay.

As indicated previously, the probe and instrumentation may be adapted for the detection of a wide range of trace volatiles, for example those emitted by live pests such as rats, cockroaches and termites, and indeed any other trace volatiles resultant from environmental decay or infestation, or any other natural or synthetic chemical process.

The invention claimed is:

1. An instrument for detecting the presence of trace volatiles, comprising a sampling probe having a receptor adapted protectively to receive a coated fibre of a solid phase micro-extraction device (SPME) for introduction to a site to be sampled, the sampling probe including means associated with the receptor to direct a fluid stream from the site over the SPME fibre located within the receptor thus to cause one or more trace volatiles to be captured by the fibre coating, and the instrument further comprising a data acquisition device having an array of gas sensors contained within a chamber adapted to receive said coated SPME fibre having one or more trace volatiles captured thereby, means for causing said one or more trace volatiles to be released from the fibre coating into the chamber such that in use the gas sensors may detect said one or more trace volatiles released from the SPME fibre, and means responsive to the sensors to produce one or more signals identifying said one or more trace volatiles captured by and released from the SPME fibre.

2. An instrument according to claim 1, wherein the receptor is maintained at ambient temperature during capture of said one or more trace volatiles.

3. An instrument according to claim 1, wherein the gas sensors are metal oxide semi-conductor gas sensors which, in use, undergo individual changes and electrical resistance representative of said one or more trace volatiles.

4. An instrument according to claim 1, wherein the sampling probe includes a dust or other contaminant filter to prevent such contaminants from alighting upon the SPME fibre coating and to prevent non-specific capture and loss of trace volatiles of interest for the detection procedure.

5. An instrument according to claim 1, wherein the receptor includes a fibre guide to centralise the SPME fibre within a tubular barrel.

6. An instrument according to claims 4 or 5, wherein the receptor includes a fibre guide to centralize the SPME fibre within a tubular barrel which barrel which includes a threaded portion for attachment of the contaminant filter or, selectively, of an additional length of barrel.

7. An instrument according to claim 1, wherein the fluid stream direction means includes a pump connected to the receptor.

8. An instrument according to claim 1, wherein the receptor is formed as a housing adapted removably to receive the SPME device.

9. An instrument according to claim 8, wherein the housing includes means therein to manoeuvre the SPME fibre thus to advance and retract the fibres selectively within the receptor.

10. An instrument according to claim 1, wherein the means for causing said one or more trace volatiles to be released from the SPME fibre comprises a plurality of individual heaters each associated with one of the gas sensors.

11. An instrument according to claim 1, including means automatically to retract the fibre within a needle sheath of the SPME device prior to or upon removal from the receptor.

12. An instrument according to claim 1, including means, where samples are to be taken at a plurality of locations, to link or identify an SPME fibre, after sampling, with an associated sampling probe or location thereof.

13. An instrument according to claim 1, including means to determine and record the duration of a sampling period and/or of the number of samples taken by an individual SPME fibre.

14. A method of detecting the presence of trace volatiles, comprising the steps of introducing a coated SPME fibre contained protectively within a receptor of a sampling probe, to a site to be sampled, and directing a fluid stream over the SPME fibre within the receptor thus to cause any trace volatiles present at the site to be captured by the fibre coating; introducing the SPME fibre into a data acquisition device having a chamber containing an array of gas sensors; causing one or more captures trace volatiles to be released from the SPME fibre; and producing one or more signals identifying said one or more trace volatiles captured by and released from the SPME fibre.

* * * * *